(12) United States Patent
Sawyer

(10) Patent No.: US 6,401,724 B1
(45) Date of Patent: Jun. 11, 2002

(54) METHOD OF APPLYING A COSMETIC NAIL LACQUER OR POLISH TO A NAIL

(75) Inventor: Kenneth I. Sawyer, Stamford, CT (US)

(73) Assignee: Par Pharmaceuticals Incorporated, Spring Valley, NY (US)

( * ) Notice: Subject to any disclaimer, the term of this patent is extended or adjusted under 35 U.S.C. 154(b) by 0 days.

(21) Appl. No.: 09/685,364

(22) Filed: Oct. 10, 2000

Related U.S. Application Data

(60) Provisional application No. 60/158,721, filed on Oct. 11, 1999.

(51) Int. Cl.⁷ .............................................. A45D 29/00
(52) U.S. Cl. ...................................................... 132/200
(58) Field of Search .................... 132/73, 200; 424/401, 424/61

(56) References Cited

U.S. PATENT DOCUMENTS

| | | |
|---|---|---|
| 2,683,730 A | 7/1954 | Seeger et al. |
| 2,888,439 A | 5/1959 | Simons |
| 3,004,896 A | 10/1961 | Heller et al. |
| 3,189,615 A | 6/1965 | Heller et al. |
| 3,394,164 A | 7/1968 | McCellan et al. |
| 4,328,322 A | 5/1982 | Baron |
| 4,328,325 A | 5/1982 | Marquardt et al. |
| 5,319,058 A | 6/1994 | Hattori et al. |
| 5,346,692 A * | 9/1994 | Wohlrab et al. ............... 424/61 |
| 5,516,873 A | 5/1996 | Hicks et al. |
| 5,643,581 A * | 7/1997 | Mougin et al. ............. 424/401 |
| 5,968,986 A * | 10/1999 | Dyer ............................ 424/61 |
| 5,993,790 A * | 11/1999 | Strauss ........................ 424/61 |
| 6,013,677 A * | 1/2000 | Dyer ............................ 424/61 |
| 6,156,325 A * | 12/2000 | Farer et al. .................. 424/401 |
| 6,162,420 A * | 12/2000 | Bohn et al. ................... 424/61 |
| 6,224,887 B1 * | 5/2001 | Samour et al. ............. 424/401 |

FOREIGN PATENT DOCUMENTS

EP  0 630 666  11/1998

* cited by examiner

*Primary Examiner*—Todd E. Manahan
(74) *Attorney, Agent, or Firm*—Jerome Rosenstock; Frommer Lawrence & Haug LLP

(57) ABSTRACT

A method of applying a cosmetic nail lacquer or polish to a nail of an animal is disclosed. The method comprises applying a polyurea composition to the nail. Such nail composition is selected from a reaction solution, a stabilized reaction solution, a blocked reaction solution or a mixture of any of the foregoing solution.

17 Claims, No Drawings

METHOD OF APPLYING A COSMETIC NAIL LACQUER OR POLISH TO A NAIL

This application claims priority from U.S. provisional application Serial No. 60/158,721 filed Oct. 11, 1999, which is incorporated herein by reference.

BACKGROUND OF THE INVENTION

1. Field of the Invention

This invention relates to a method of applying a cosmetic nail lacquer or polish to a nail and, more particularly, to a method utilizing a polyurea composition by topical administration thereof to form a coat upon which the lacquer or polish is applied.

2. Description of the Prior Art

The commercial lacquers and nail polishes which are presently used, especially for cosmetic purposes, have a tendency to chip, flake or crack from the nails to which they are applied and upon long duration adversely affect the underlying nail. Accordingly, what is desired is a treatment or a base coating used in conjunction with currently available cosmetic polishes and lacquer coatings which strengthens these coatings and prevents cracking or chipping or injury to the underlying nail.

SUMMARY OF THE INVENTION

This invention relates to a method of applying a cosmetic nail lacquer or polish to a nail and, more particularly, to a method of utilizing a polyurea composition by topical administration thereof to the affected nail.

The method comprises applying a polyurea composition selected from (a) a reaction mixture comprising a first component of an oligomeric amino benzoic acid ester or amide having the formula

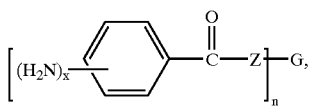  (I)

where n is an integer from 2 to 4; each x is one or two; each benzoyl nucleus is para. meta, or di meta amino-substituted; each Z is —O— or —N—; and G is an n-valent radical obtained by removal of hydroxy groups or amino groups from an n-valent polyol or polyamine having a molecular weight of from about 400 to about 6,000; and a second component comprising a polyisocyanate; (b) a stabilized reaction mixture comprising the first component of the oligomeric amino benzoic acid ester or amide of formula I, combined with the second component of the polyisocyanate in a stabilizing carrier; (c) a blocked reaction mixture, comprising the first component of formula I having at least one of its aromatic amino groups blocked by a reaction with an aldehyde, combined with the second component, polyisocyanate; and (d) a mixture of any the foregoing.

DETAILED DESCRIPTION

A suitable first component is selected from among an oligomeric amino benzoic acid ester or amide and an aromatic diamine derivative. The oligomeric amino benzoic acid ester or amide has the formula,

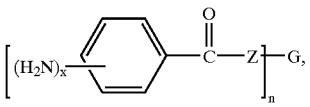  (I)

wherein n is an integer of from 2 to 4; each x is one or two; each benzoyl nucleus is para-, meta- or di-meta amino substituted; each Z is

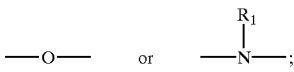

and G is an n-valent radical obtained by the removal of hydroxyl groups or amino groups, respectively, from an n-valent polyol or polyamine having a molecular weight of from about 400 to about 6,000. It will be appreciated that the characterization of radical G (as an n-valent radical which may be obtained by the removal of hydroxyl groups or amino groups, respectively, from an n-valent polyol or polyamine) is set forth for convenience in defining the nature of radical G per se, notwithstanding that abstraction or removal of hydroxyl or amino groups from such polyol or polyamine is not mechanistically involved in the synthesis or production of the oligomeric aminobenzoic acid esters and amides thereof; and $R_1$ is hydrogen $C_1$–$C_{20}$alkyl, [($C_1$–$C_{20}$ alkoxy)aryl]methyl or [C1–C20 alkyl)aryl]methyl.

It will be seen from inspection of the formula I set forth hereinbefore that the oligomeric aminobenzoic acid esters utilized in the present invention comprise di-, tri- and tetra-(aminobenzoate) esters of oligomeric polyol materials where n is, respectively, 2, 3 or 4. Correspondingly, oligomeric aminobenzoic acid amides comprise di, tri- and tetra-(aminobenzoic acid) amides of oligomeric polyamine materials where n is respectively 2, 3, or 4. Inasmuch as the aromatic rings of the benzoyl moieties of the esters and amides each contain one or two amino groups, the oligomeric amino benzoic acid esters and amides may be termed oligomeric polyamines. Accordingly, the term "oligomeric polyamine" can be utilized in reference to the essential aminobenzoic acid ester or amide components of the poly addition product and process of the present invention.

The oligomeric aminobenzoic acid esters utilized in the practice of the poly addition process of the present invention are aminobenzoate esters of oligomeric polyol materials and can be conveniently provided by reaction of a nitro-substitued benzoyl halide, or a nitro-substituted benzoic acid, with a suitable polyol, such as polyalkylene ether or ester polyol, followed by reduction of the nitro groups of the resulting product to the corresponding amino groups. Thus, for example, an oligomeric di-(p-aminobenzoate) ester useful herein can be prepared by reaction of two moles of p-nitrobenzoyl chloride with one mole of a dihydric alcohol such as poly(ethylene glycol) having a molecular weight in the range of from about 400 to about 6,000 and by reduction of the resulting poly(ethylene glycol) di(p-nitrobenzoate) etc.

In like manner, oligomeric aminobenzoic acid amides useful herein can be provided by reaction of a nitro-substituted benzoyl halide, or a nitro-substituted benzoic acid, with a suitable polyamine, followed by a reduction of the benzoyl halide or benzoic acid nitro-substitutes to corresponding amino groups. For example, an oligomeric di(p-aminobenzoic acid) amide useful herein can be prepared by reaction of two moles of p-nitrobenzoic acid with one mole of an oligomeric diamine such as propoxlated propylene diamine having a molecular weight in the range of from about 400 to 6,000 and by reduction of the nitro groups to amino groups.

The nature of radical G of the aminobenzoic acid esters and amides can vary and will depend upon the nature of the oligomeric polyol and polyamine materials utilized in the preparation thereof. As indicated previously, the radical G will be derived from a polyol or polyamine material having a molecular weight of from about 400 to about 6,000. Preferably, the polyol or polyamine will have a molecular weight in the range of about 650 to 2,000. The radical G can comprise an n-valent saturated or unsaturated, straight chain or branched chain hydrocarbon radical which can be interrupted by oxygen ether atoms. For example, where a polyether polyol or a polyether polyamine is utilized in the preparation of an oligomeric aminobenzoic acid or amide, the corresponding G radical will comprise repeating oxygen ether atoms. Preferably, radical G will include such oxygen ether atoms.

It will be appreciated from inspection of the hereinbefore described representative formula I that the nature of n-valent radical G will vary with the value of integer n. Thus, where n is two, radical G will be a divalent radical —G— obtained by removal or abstraction of two hydroxyl or amino groups, respectively, from an oligomeric polyol or polyamine having a molecular weight of from about 400 to about 6,000. In the case where n is three, G will represent a trivalent radical

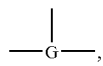

obtained by removal of three hydroxyl or amino groups from a polyol or polyamine having a molecular weight in the same range. Similarly, when n is four, radical G will represent a tetravalent radical.

obtained by removal of four hydroxyl or amino groups from a polyol or polyamine having a molecular weight in the same range.

The Z moieties of the oligomeric aminobenzoic acid ester and amide compounds hereof can independently be oxygen or imino groups and, accordingly, each Z is defined as being

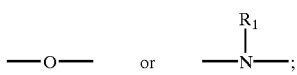

While the utilization of, for example, an oligomeric polyol or polyamine having, respectively, only hydroxyl or amino group will be preferred from the standpoint of convenience and ease of preparation, compounds having both hydroxyl and amino groups can be utilized for the preparation of mixed aminobenzoic acid ester/amide compounds hereof.

A number of polyol materials can be suitably employed for the preparation of the oligomeric aminobenzoic acid esters utilized herein. Examples of such polyols, which provide divalent, trivalent or tetravalent G radicals include oligomeric diols, such as polyalkyleneether glycols and polyalkylene-arylene-ether glycols; oligomeric triols, such as the polyalkyleneether glycerols or mixed polyalkyene-arylene-ether glycerols; and oligomeric tetrols, such as the polyalkylene ether pentaerythriols or mixed polyalkylene-arylene-ester pentaerythritols.

A preferred class of polyol materials useful in the preparation of the aminobenzoic acid esters herein comprises the polyalkyleneether glycols which provide a divalent G radical and which may be represented by the formula $HO(RO)_a$ wherein R is an alkylene radical containing up to ten carbon atoms and a is an integer sufficient to provide a molecular weight within the range of from about 400 to 6,000, and preferably, from about 650 to about 2,000. Preferably R is an alkylene radical of from 2 to 4 carbon atoms. Examples of polyalkyleneether glycols useful herein include polyethyleneether glycol, polypropylene ether glycol, polyhexyleneether glycol, polytetramethyleneether glycol, polydecamethyleneether glycol, poly-1,2-dimethyl ethyleneether glycol and the copolymer of tetrahydrofuran and 1-allyloxy-2,-3-epoxypropane. The polyalkyleneether glycols herein can be readily obtained, for example, by polymerization to suitable molecular weight of an alkylene ether, e.g., ethylene oxide, tetrahydrofuran, propylene oxide, or, an admixture thereof, in the presence of water or other low molecular weight alcohol or hydrogen-donor compound.

The polyalkylene-arylene-ether glycols can also be employed for the preparation of oligomeric p-aminobenzoic acid esters utilized herein. These glycols, similar in structure to the polyalkyleneether glycols, additionally contain arylene radicals. Thus, arylene groups such as phenylene, naphthalene and anthracene radicals can be present in the polyalkylene-arylene-ether glycols. In general, the arylene groups will be present in minor proportion relative to the alkylene groups. Normally, the glycol will contain at least one polyalkyleneether radical of molecular weight of about 500 for each arylene radical.

Another class of polyol materials suited to the preparation of oligomeric aminobenzoic acid esters useful herein comprises the class of hydroxy-containing hydrocarbon polymer materials having a molecular weight in the range of from about 400 to 6,000. Accordingly, the radical G derived therefrom will comprise an n-valent saturated or unsaturated, straight or branched chain hydrocarbon radical which may be obtained by removal of hydroxyl groups from a saturated or unsaturated straight or branched chain hydrocarbon polymer having a molecular weight within the previously set forth range. Preferably, the n-valent G radical will be an aliphatic hydrocarbon radical derived from an aliphatic hydrocarbon polyol. Examples of suitable hydrocarbon polyol materials include the polyols obtained from the polymerization of polymerizable ethylenically unsaturated monomers, such as 1,4-butadiene, and by the introduction of hydroxyl groups in known manner. Such polyol materials are known and can be prepared, for example, by free-radical initiated polymerization of a polymerizable ethylenically-unsaturated monomer to provide a dicarboxylate-substituted hydrocarbon polymer, for example, a dicarboxylate-terminated polymer. Reduction in known manner provides an aliphatic hydrocarbon polyol, for example, an aliphatic hydrocarbon diol. A suitable method for the production of such polyol materials is described in greater detail in U.S. Pat. No. 2,888,439 which is incorporated by reference hereinto in its entirety.

As indicated previously, the polyol materials useful for the preparation of the oligomeric aminobenzoic acid esters utilized herein also include polyols capable, by abstraction, respectively, of three or four hydroxyl groups, of providing a trivalent or tetravalent radical G. Thus, polyalkyleneether polyols and mixed polyalkylene-arylene-ether polyols derived from such polyhydric alcohols as glycerol, trimethylolpropane, pentaerythritol and the like can be employed. Such materials can be obtained by oxyalkylation as, for example, by reaction of glycerol or pentaerythritol with ethylene oxide, propylene oxide or a mixture thereof. The resulting trifunctional and tetrafunctional ethers may be advantageously employed for the preparation of oligomeric tri- and tetra-(aminobenzoate) esters which can be suitably employed for the production of polymers having increased cross-linking.

A variety of polyamines can be utilized for the preparation of oligomeric aminobenzoic acid amides useful herein. Examples of such polyamines, which provide divalent, trivalent or tetravalent G radicals include oligomeric diamines, triamines and tetramines. For example, oligomeric diamines useful for the provision of oligomeric aminobenzoic acid amides include polyamines of the formula

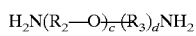

wherein each of $R_2$ and $R_3$ is a divalent saturated or unsaturated, straight chain or branched chain hydrocarbon radical; c is zero or an integer; d is an integer; and the combined value of c and d is such as to provide a molecular weight for the polyamine of from about 400 to about 6,000. Preferably, each of $R_2$ and $R_3$ is an aliphatic, straight or branched chain divalent hydrocarbon radical, e.g., an alkylene radical of from 2 to 10 carbon atoms, and more preferably from 2 to 4 carbon atoms. Suitable polyamines are known and commercially available and can be obtained, for example, by polymerization of an alkylene oxide and conversion of terminal hydroxyl groups to amino groups by known amination techniques.

The polyol and polyamine materials from which the n-valent G radical is derived can contain substituent moieties where such substituents do not interfere with the desired reaction of the aminobenzoic acid ester or amide with an isocyanate. Alkyl or halo substituents, for example, can be suitably present. The n-valent G radical can also contain repeating oxygen ether atoms as will be the case where the polyol or polyamine from which radical G is derived comprises, for example, a polyalkyleneether glycol, a polyalkyleneether glycerol, a polyalkyleneether pentaerythritol, a mixed polyalkylene-arylene-ether polyol or an amine-terminated polyalkylether. The polyol and polyamine materials can additionally contain ester linkages. Thus, polyol materials of suitable molecular weight, i.e., in the range of from about 400 to 6,000, ester linkages as may be obtained, for example, by reaction of a polycarboxylic acid and a polyhydric material can be suitably employed. An example of such a polyol having ester groups include the oligomeric polyester polyols such as may be obtained by the condensation of adipic acid and ethylene glycol.

The oligomeric aminobenzoic acid esters utilized herein for the production of polymeric products include the di-(aminobenzoate)esters(obtained, for example, by reaction of two moles of a nitro-substituted benzoyl chloride with one mole of an oligomeric glycol having a molecular weight of about 400 to about 6,000, followed by reduction of nitro-to-amino-groups); and the tri-(aminobenzoate)esters(from three moles of nitro-substituted benzoyl chloride and one mole of an oligometric triol of molecular weight of about 400 to about 6,000, followed by reduction of nitro-to-amino-groups). Similarly, the oligomeric aminobenzoic acid esters include the tetra-(aminobenzoate) esters derived from four moles of a nitro-substituted benzoyl chloride per mole of an oligomeric tetrol of molecular weight of about 400 to about 6,000, followed by a suitable nitro-to amino group reduc tion. These oligomeric aminobenzoate esters can conveniently be represented by the following formulae:

Formula II

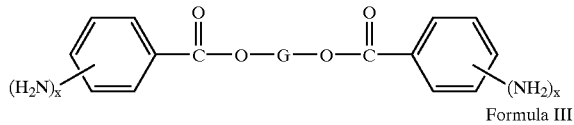

Formula III

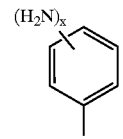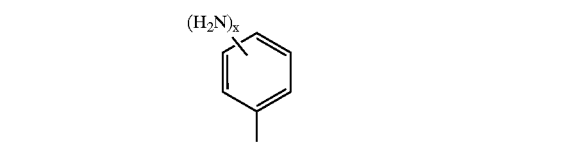

Formula IV

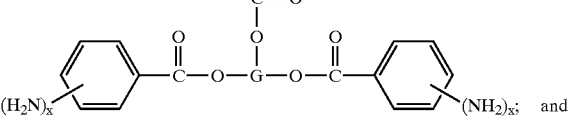
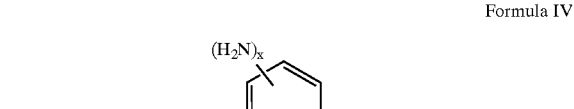
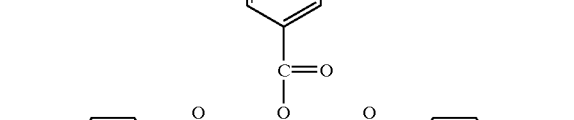

Similarly, the oligomeric aminobenzoic acid amides utilized herein for the production of polymeric products include the di-(aminobenzoic acid) amides, the tri-(aminobenzoic acid) amides and the tetra-(aminobenzoic acid) amides. These oligomeric aminobenzoic acid amides can conveniently be represented by the following formulae:

Formula V

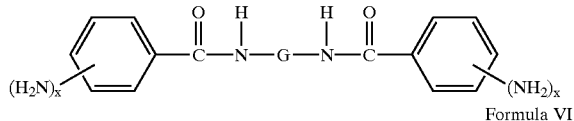

Formula VI

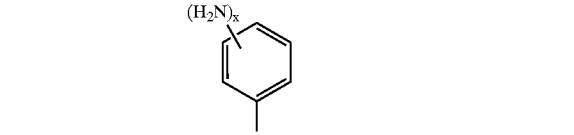
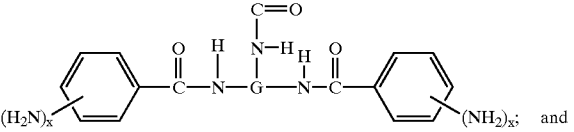

Formula VII

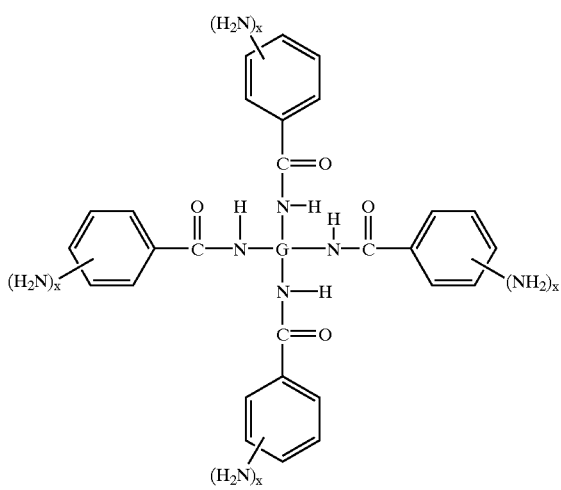

In the formulae shown for the oligomeric aminobenzoate esters hereof (Formulae II, III, and IV) and the oligomeric aminobenzoic acid amides (Formulae V, VI, and VII), G will represent, respectively, a divalent, trivalent or tetravalent radical derived from a polyol or polyamine having a molecular weight in the range of about 400 to about 6,000, and preferably, in the range of from about 650 to about 2,000. As will be apparent from inspection of each of the formulae set forth hereinbefore, the phenyl group of each benzoyl moiety contains one or two amino groups depending upon the value of each x as one or two. The amino groups are positioned such that each benzoyl nucleus is para-amino-substituted, a meta-amino-substituted or di-meta-amino-substituted. Accordingly, the oligomeric aminobenzoic acid esters and amides hereof are inclusive of para-amino-benzoic acid esters and amides, meta-aminobenzoic acid esters and amides; and di-meta-aminobenzoic acid esters. It will be appreciated that each benzoyl moiety of an oligomeric aminobenzoic acid ester or amide hereof, while para-, meta- or di-meta-amino-substituted, need not be identically substituted. Preferred oligomeric aminobenzoic acid esters and amides herein are those wherein the benzoyl moieties are each para-amino substituted. In addition to the amino-group substitution of the benzoyl moieties, the benzoyl groups can be substituted with non-interfering groups. Accordingly, the benzoyl moieties of the aminobenzoic acid ester and amide compounds hereof can be substituted with halogen, alkyl or other substituents which do not interfere with the desired polyisocyanate addition process.

Examples of oligomeric aminobenzoic acid esters useful herein and represented by Formula I include the following wherein a and b are integers having values corresponding to molecular weights for the polyols from which they are derived of from about 400 to about 6,000.

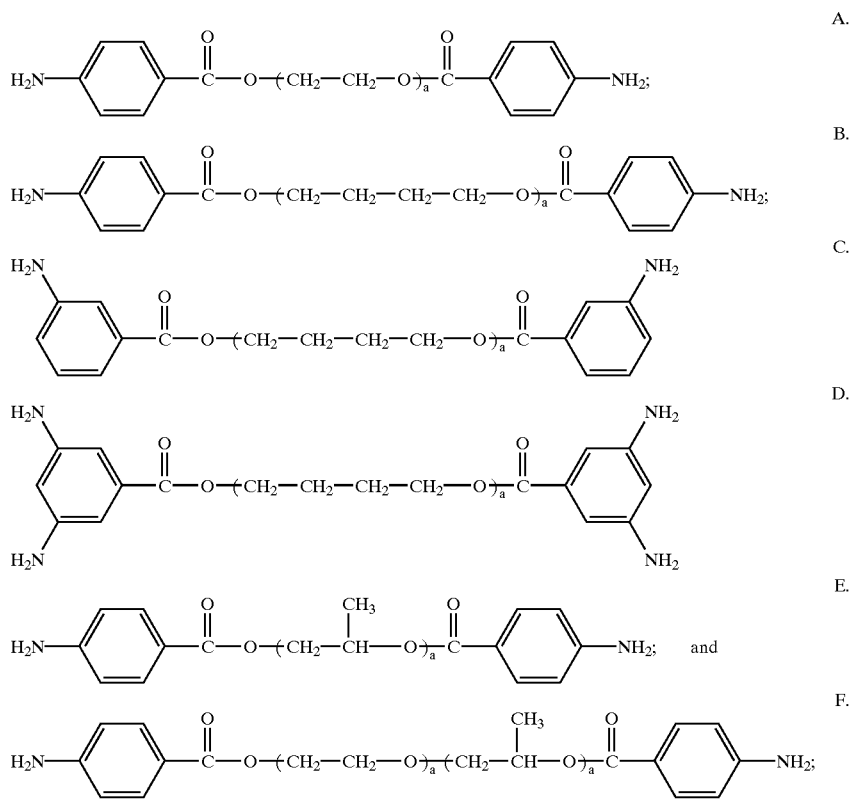

An example of a compound of Formula (II) B., above, is VERSALINK™ P 1000, commercially available from Air Products & Chemicals, Inc. which has the formula

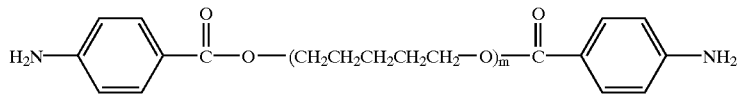

Where m=13–14, with a molecular weight of 1238.

Other commercially available products include VERSALINK™ P-650, having an average molecular weight of 830, and VERSALINK™ 250, having an average molecular weight of 485.

Examples of oligomeric aminobenzoate esters useful herein and represented by Formula III include the following wherein a and b are integers having values corresponding to the molecular weights for the polyols from which they are derived of from about 400 to about 6,000.

G.

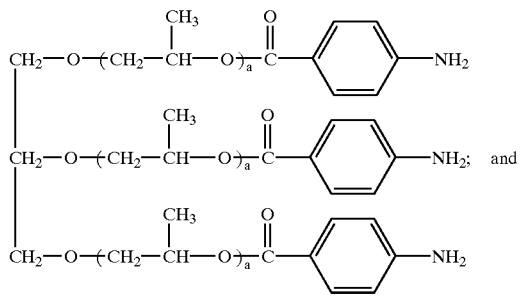

H.

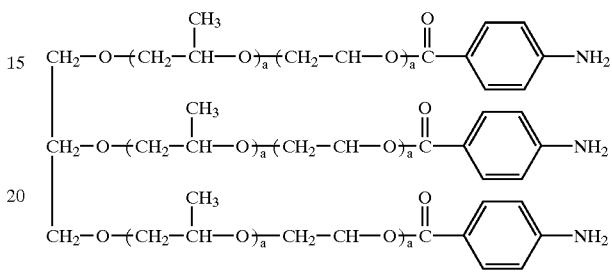

An example of an oligomeric aminobenzoate ester represented by Formula IV includes the following wherein each a is an integer having a value corresponding to a molecular weight for the polyalkyleneether pentaerythritol from which the aminobenzoate ester is derived of from about 400 to about 6,000.

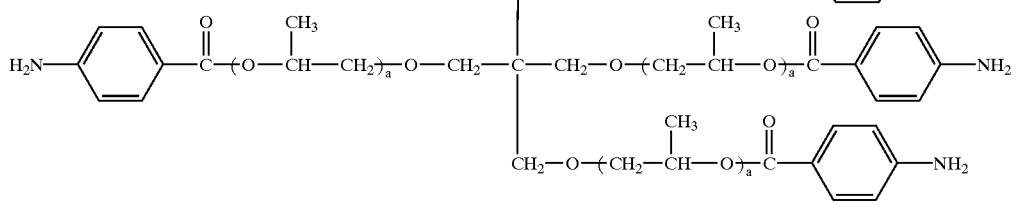

Examples of oligomeric aminobenzoic acid amides useful herein and represented by Formula V include the following wherein each c is an integer having values corresponding to molecular weights for the polyamines from which they are derived of from about 400 to about 6,000.

J.

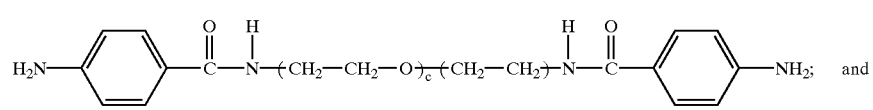

and

K.

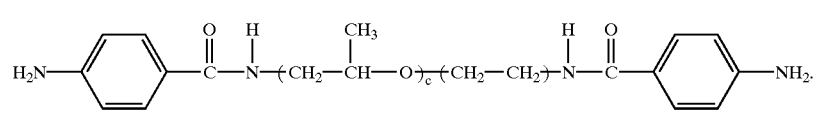

An example of an oligomeric aminobenzoic acid amide useful herein and represented by Formula VI is the following wherein each c has a value corresponding to the molecular weight for the polyamine from which the amide is derived of from about 400 to about 6,000.

L.

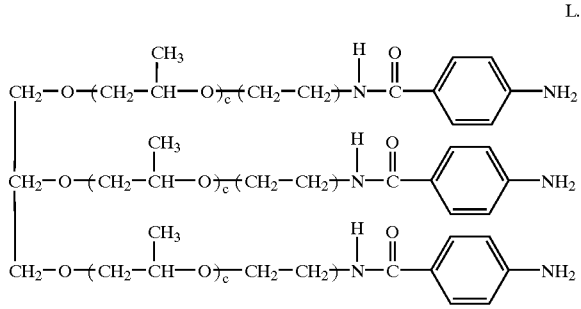

An example of an oligomeric aminobenzoic acid amide represented by Formula VII includes the following wherein c is an integer having a value corresponding to a molecular weight for the polyamine from which the amide is derived of from about 400 to about 6,000.

The above-described oligomeric aminobenzoic acid esters and amides and their preparation is described in U.;S. Pat. Nos. 4,328,322, 5,039,775 and EP 0630666) 630666 which are incorporated by reference hereinto in their entirety for all purposes.

Examples of other aminobenzoate esters or amides include,
polyethyleneglycol bis(4-aminobenzoate);
polyethyleneglycol bis(2-aminobenzoate);
polyethyleneglycol bis(3-aminobenzoate);
polytetramethyleneglycol bis(4-aminobenzoate);
polytetramethyleneglycol bis(2-aminobenzoate);
polypropyleneglycol bis(4-aminobenzoate);
polypropyleneglycol bis(2-aminobenzoate);
poly(oxyethylene-oxypropylene)glycol bis(4-aminobenzoate);
polyoxybutyleneglycol bis(4-aminobenzoate);
polytetramethyleneglycol bis(3,5-diaminobenzoate);
polypropyleneetherglycerol tris(4-aminobenzoate);
polypropyleneetherpentaerithritol tetrakis(4-aminobenzoate);
polyoxyethylene bis( 4-aminobenzamide);
polyoxypropylene bis(4-aminobenzamide);
polyoxypropylene bis(3,5-diaminobenzamide); and
polyoxypropyleneetherglycerol tris(4-aminobenzamide); as revealed in U.S. Pat. No. 5,319,058, incorporated by reference hereinto in its entirety.

A suitable polyisocyanate is selected. A suitable polyisocyanate is one which is conventionally employed in the production of polyurethanes.

Examples of monomeric polyisocyanates useful herein include polyisocyanates and polyisothiocyanates which are PAPI-1(a polyaryl polyisocyanate as defined in U.S. Pat. No. 2,683,730), tolylene diisocyanate "TDI", triphenylmethane-4,4'4"-triisocyanate, benzene-1,3,5-triisocyanate, toluene-2, 4,6-triisocyanate, diphenyl-2,4,4'-triisocyanate, hexamethylene diisocyanate, xylylene diisocyanate, chlorophenylene diisocyanate, diphenylmethane-4,4,'-diisocyanate, naphthalene-1, 5-diisocyanate, xylene-alpha,alpha'-disothiocyanate, 3,3'-dimethyl-4, 4' biphenylene diisocyanate, 3-3' dimethoxy-4, 4'-biphenylene diisocyanate,2',3,3'-dimethyl-4,4'-biphenylene diisocynate, 5,5'-tetramethyl-4, 4' biphenylene diisocyanate, 2,2', 5,5'- tetramethyl-4,4' biphenylene diisocyanate, 4,4' methylenebis (phenylisocyanate), 4,4'-sulfonylbis (phenylisocyanate), 4,4'-methylene di-orthotolylisocyanate, ethylene diisocyanate, ethylene diisothiocyanate, trimethylenediisocyanate and the like. Mixtures of any one or more of the above mentioned organic isothiocyanates or isocyanates may be used as desired.

Additionally, suitable are mixtures of TDI such as a mixture (80/20 by weight) of 2,4-toluene diisocyanate and 2,6 toluene diisocyanate or a mixture (65/35 by weight) of 2,4-toluene diisocyanate and 2,6-toluene diisocyanate; tetramethylene diisocyanate; hexamethylene diisocyanate; xylene diisocyanate; 1,5-napththylene diisocyanate; 1,4-phenylene diisocyanate; 4,4'-' diphenylmethane diisocyanate (MDI) (Upjohn's ISONATE® 125M); 4,4'4"-triphenylmethane triisocyanate; and 3,3'-dimethyl-4,4'-diphenylmethane diisocyanate. Aliphatic diisocyanates such as the $C_{36}$ aliphatic diisocyanate derived from the dimer of ricinoleic acid can be suitably employed and are commercially available, for example, as DDI-1410 (Henkel Corporation, Resin Division, Minneapolis, Minn.). The polyisocyanates hereof are known polyisocyanates in the field of polyurethane technology and can be employed singly or in admixture. Other examples of such polyisocyanates can be found, for example, in *The Development and Use of Polyurethane Products*, E. N. Doyle, McGraw-Hill Book Company, page 27 (1971), and *Polyurethane Handbook*, $2^{nd}$ Ed., Gunter Oertel Hauser, Gardner Press (1994).

Preferred polyisocyanates for employment in the process of the present invention are polyisocyanate materials in a liquid form at ambient temperatures e.g. a liquid MDI product as disclosed in U.S. Pat. No. 3,394,164. These materials facilitate the production of polymeric products from normally liquid oligomeric aminobenzoic acid esters or amides and obviate the requirement of melting a solid polyisocyanate as a prerequisite to providing a suitable reaction mixture. Suitable liquid polyisocyanate materials are known and include, for example, polymeric MDI (4,4'-diphenylmethane diisocyanate) products obtained as by-products from the synthesis of MDI.

In the production of MDI by the condensation of aniline with formaldehyde and the conversation of amino to corresponding isocyanate groups, a content of the initially formed bis-adduct of aniline and formaldehyde reacts further with the reaction mixture to form polymeric aniline derivatives which are in turn converted to isocyanates. Typically, such polymeric derivatives will have a functionality of from about 4 to about 15, for example, about 10 isocyanate groups per molecule. Products containing such polymeric polyisocyanates in the form of a pot residue after removal of pure MDI by distillation can be utilized. Similarly, polyisocyanate products comprising such polymeric polyisocyanate species in admixture with pure MDI, i.e., the undistilled reaction mixture, can be employed. Polymeric MDI products can be employed herein to advantage and are commercially available under such trade designations as RURBINATE® M, RUBINATE® LF-168 and RUBINATE® LF-209 (available from Rubicon Chemicals Inc., Geisman, La.) and PaPI 27, PaPI 135, PaPI 580 and PaPI 901 (available from the Upjohn Company, Kalamazoo, Mich.).

Another liquid polyisocyanate material which can be employed where cross-linking is desirably introduced into the polymeric products hereof comprises an admixture of MDI and a tri-functional cycloaddition product of MDI. An admixture of MDI and a tri-functional cycloadduct having the following structure, where R is

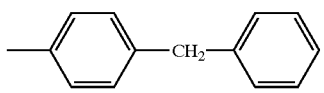

can be employed:

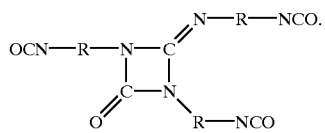

Such an admixture is available under the designation "Liquid MDI", Isonate® 2143L, (Dow Chemical, Midland, Mich.).

To reiterate, in addition to the preferred MDI, modified forms of monomeric MDI or MDI-containing resins, any suitable organic diisocyanate may be used in the process of this invention such as, for example, aliphatic diisocyanates, aromatic diisocyanates, alicyclic diisocyanates, and heterocyclic diisocyanates including such as, for example, ethylene diisocyanate, ethylidene diisocyanate, propylene diisocyanate, butylene diisocyanate, cyclopentylene-1,3-diisocyanate, cyclohexylene-1,4-diisocyanate, cyclohexylene-1,2-diisocyanate, 2,4-tolylene diisocyanate, 2,6-tolylene diisocyanate, 4,4'-diphenylmethane diisocyanate, 2,2-diphenylpropane-4,4'-diisocyanate, p-phenylene diisocyanate, m-phenylene diisocyanate, xylylene diisocyanate, 1,4-napthylene diisocyanate, 1,5-naphthylene diisocyanate, diphenyl-4,4' diisocyanate, azobenzene-4,4'-diisocyanate, diphenylsulfone-4,4'-diisocyanate, dichlorohexamethylene diisocyanate, tetramethylene diisocyanate, pentametylene diisocyanate, hexamethylene diisocyanate, 1-chloroboenzene-2,4-diisocyanate, furfurylidene diisocyanate, triphenyl methane triisocyanate and the like.

Other examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4' dicyclohexyl-methane diisocyanate, 1,3- and 1,4-bis(isocyanatomethyl)-cyclohexane, bis-(4-isocyanato-3-methyl-cyclohexyl)-methane, α,α,α',α'-tetramethyl-1,3-1-isocyanato-1-methyl-4(3)-isocyanatomethyl cyclohexane, 2,4-, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof. Aromatic polyisocyanates containing 3 or more isocyanate groups such as 4,4',4"-triphenylmethane diisocyanate.

In accordance with the present invention the polyisocyanate component can be in the form of an NCO prepolymer or a polyisocyanate adduct, more preferably a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight. The isocyanato-isocyanurates generally have an average NCO functionality of 3 to 3.5 and an NCO content of 5 to 30%, preferably 10 to 25% and most preferably 15 to 25% by weight.

Preferred polyisocyanate adducts are the polyisocyanates containing isocyanurate groups, biuret groups or mixtures of isocyanurate and allophanate groups.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular p weights of 400 to about 6,000, preferably 800 to about 3,000, and optionally low molecular weight compounds with molecular weights below 400. The molecular weights are number average molecular weights ($M_n$) and are determined by end group analysis (OH number).

With regard to the organic diisocyanes, the prepolymers and the polyisocyanate adducts, reference is made to U.S. Pat. No. 5,516,873, which is incorporated by reference hereinto in its entirety.

The first and second components are combined just prior to the application to a nail in substantially equivalent proportions to form the liquid reaction solution. By "substantially equivalent" refers to the utilization, in general, of an amount of polyisocyanate component or reactant of about 0.9 to 1.2 equivalents per equivalent of the first component, i.e. the oligomeric aminobenzoic acid ester or amide, based upon the isocyanate groups and amino groups, respectively of the polyisocyanate and oligomeric amino benzoic acid ester or amide reactants. Preferably, from about 1.0 to about 1.15 equivalent of polyisocyanate material per equivalent of ologomeric aminobenzoic acid ester or amide is employed.

In practice, the reaction solution is applied to a nail by any conventional topical means, e.g. brushing, swabbing, spraying, etc., until a liquid film or layer of a suitable thickness, is formed. The reaction mixture containing liquid film penetrates the nail, sufficient to a depth and the first and second components chemically react, typically after five to fifteen minutes, to polymerize to form a polyurea coat on the treated nail. The cure time can be reduced by applying heat to the nail, e.g. with a heating lamp, to affect the therapeutic polyurea coat.

After the polyurea coat is formed on the nail, any commercial nail lacquer or polish, such as acrylic, methacrylic, etc., can then be applied over the polyurea coat to form a nail lacquer or polish cosmetic coat. The resultant cosmetic coat upon drying is one which is waterproof and strengthened whereby it will not crack, flake or peel off. Most importantly after prolonged covering, e.g. 1 to 3 mils of the nail (over the base polyurea coat), the underlying nail will not be damaged or injured.

In another embodiment, a stabilized reaction solution is utilized as a polyurea composition. A first component is selected from the oligomeric amino benzoic acid ester or amide of formula I or an aromatic diamine derivative, which is combined with the polyisocyanate second component in a suitable stabilizing carrier to form a stabilized reaction solution destined to be used to treat the nail for cosmetic purposes.

A suitable aromatic diamine derivative includes (a) an aromatic diamine of the formula,

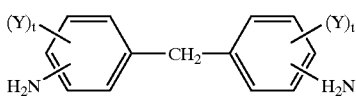

(1)

where each Y is independently from one another H, loweralkyl, loweralkoxy, halogen and $CF_3$, where the term "lower" means the group it is describing contains from 1 to 6 carbon atoms; where the term "alkyl" refers to a straight or branched chain hydrocarbon containing no unsaturation, e.g. methyl, ethyl, isopropyl, 2-butyl, neopentyl, n-hexyl, etc; where the term "alkoxy" has the formula loweralkyl-O—; and t is an integer of 1 to 4; some suitable diamines of the formula (I) include, 4,4' methylene bisaniline; 4,4' methylene bis(2-chloroaniline); 4,4' methylene bis(2,3-dichloroaniline) TCDAM); 4,4' methylene bis(2,5-dichloroaniline); 4,4' methylene bis(2-methylaniline); 4,4' methylene bis(2-ethylaniline); 4,4' methylene bis(2-isopropylaniline); 4,4' methylene bis(2,6-dimethylaniline); 4,4' methylene bis(2,6-diethylaniline); 4,4' methylene bis(2-ethyl-6-methylaniline); 4,4' methylene bis(2-chloro-6-methylaniline); 4,4' methylene bis(2-chloro-6-ethylaniline); 4,4' methylene bis(3-chloro-2,6-diethylaniline); 4,4' methylene bis(2-trifluoromethylaniline); 4,4' methylene bis(2-methyoxycarbonylaniline); and the like; (b) a diphenyl ether derivative of the formula

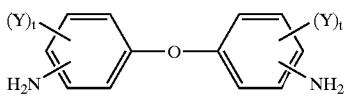

(2)

where Y and t are as previously defined; some suitable diamines of the formula (2) include 4,4' diaminodiphenyl ether; and 4,4' diamino-3,3' dichlorodiphenyl ether; (c) a diphenyl sulfone derivative of the formula

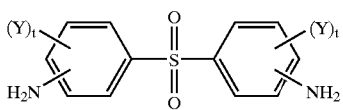

(3)

where Y and t are as previously defined; some suitable sulfone derivatives of formula (3) include, 4,4'-diaminodiphenyl sulfone; 4,4'-diamino-3,3'-dichlorodiphenyl sulfone; bis(4-aminophenoxyphenyl) sulfone; 1,2-bis(2-aminophenylthio)ethane; bis[2-(2-aminophenylthio)ethyl]terephthalate; and the like; (d), a diaminotoluene, such as 2,4-diaminotoluene; 2,6-diaminotoluene; 3,5-diethyl-2,4-diaminotoluene; 3,5-diethyl-2,6 diaminotoluene; 3,5-dimethylthio-2,4-diaminotoluene; 3,5-dimethylthio-2,6-diaminotoluene and the like; (e) a diaminodiphenyl-propane derivative of the formula

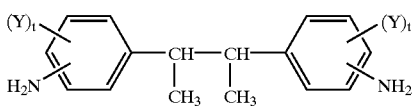

(4)

where Y and t are as previously defined; such as 2,2-bis(4-aminophenyl)propane; 2,2-bis(4-amino-3-methylphenyl) propane; 2,2-bis(4-amino-3-isopropylphenyl) propane; 2,2-bis(4-amino-3,5-dimethylphenyl) propane; 2,2-bis(4-amino-3,5-diethylphenyl) propane; 2,2-bis(4-amino-3,5-diisopropylphenyl) propane; 2,2-bis(4-amino-3-ethyl-5-methylphenyl) propane and the like; (f) an ester of an amino benzoic acid of the formula

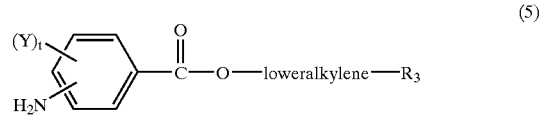

(5)

where the term "alkylene" refers to a bivalent radical of the lower branched or unbranched alkyl group it is derived from, having valence bonds from the terminal carbons thereof, e.g. ethyl (—$CH_2CH_2$—), propyl (—$CH_2CH_2CH_2$—), isopropyl ($CH_3CH$—$CH_3$), etc.; where $R_3$ is H and

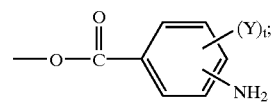

where Y and t are as previously defined; (g) 3,3' diaminobenzophenone; (h) m- or p-phenyl diamine; (i) m- or p-xylylenediamine; and (j) aromatic tetramine compounds such as 3,3',4,4'-tetraaminodiphenyl ether; 3,3',4,4'-tetraaminobiphenyl and the like; and so on. These aromatic polyamine compounds can be used either singly or as a combination of two kinds or more according to need and are disclosed in U.S. Pat. No. 5,319,058, incorporated hereinto by reference in its entirety.

The suitable stabilizing carrier is selected. A suitable stabilizing carrier is one which will completely dissolve the selected aminobenzoic acid ester or amide or the aromatic diamine derivative and the selected polyisocyanate when they are combined to form a stabilizing reaction solution but which will prevent the resultant polymeric reaction product, i.e. the polyurea, from solidifying or gelling out of the stabilized reaction solution. In other words, the stabilizing carrier either prevents the normally rapid reaction between the isocyanate group and the amino group or prevents the resultant reaction product, e.g. polyurea, from solidifying or gelling until such time as a portion of the stabilizing carrier or solvent is removed from the resultant solution, e.g., as by evaporation, thus permitting a greater time period in which to apply the resultant polyurea composition to react with and penetrate the treated nail.

A suitable stabilizing carrier comprises a stabilizing solvent selected from (a)an aldehyde or ketone of the formula

(6)

where $R_4$ and $R_5$ are independently of each other and are hydrogen and lower alkyl or $R_4$ and $R_5$ are joined to form a five or six membered ring; where the term "lower" is as previously defined; and where the term "alkyl" is as previously defined; (b) an ester having the formula

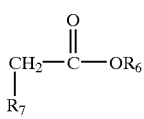
(7)

where $R_6$ and $R_7$ are loweralkyl (as previously defined) and $R_7$ additionally is H and loweralkoxy, where the term "lower" is as previously defined and the term "alkoxy" is as previously defined; (c) ortho, meta- or para-dimethylbenzene; (d) N-methylpyrrolidone; (e) Solvesso solvent, a petroleum hydrocarbon; (f) a lactone of the formula

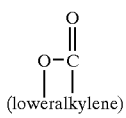
(8)

where "lower" and "alkylene" is as previously defined; such as γ-butyrolactone; and a mixture of any of the oregoing solvents; combined with at least one polyol of the formula

 (9)

where "lower" and "alkylene" are as previously defined.

Some suitable aldehydes and ketones, for example, include acetone, methyl ethyl ketone, methylisobutylketone, N-methylcyclohexanone, benzaldehyde, acetaldehyde, propionaldehyde, butryaldehyde and isobutyraldehyde. Some suitable solvents of formula (b) include methyl acetate, ethyl acetate, butyl acetate, methoxy propyl acetate and methyl ether acetate. Some suitable polyols include, for example, polyglycols of the formula

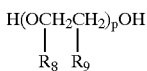
(10)

where p is an integer equal to 1 to 14, as for example when p is equal to I to 3, such compounds as ethylene glycol, propylene glycol, butylene glycols, such as 1,3-, 1,4-, and 2-3-butylene glycol, and alkylene glycols having 5 to 9 carbon atoms; when n is 4 or greater, polyglycols of an average molecular weight of about 600, such as polyethylene glycol 200, polyethylene glycol 400 and polyethylene glycol 600. It is to be understood that a mixture of the stabilizing solvents, e.g. aldehydes and ketones, can be employed, as well as a mixture of polyols, e.g., a mixture of ethylene glycol and propylene glycol.

The selected oligomeric aminobenzoic acid ester or amide or aromatic diamine derivative and the selected polyisocyanate components are added to the stabilizing carrier solution to form a stabilized reaction solution. Again, as with the reaction solution previously discussed, conventionally, these reaction components are combined in the stabilizing carrier in solution in substantially equivalent proportions, that is in amount of the polyisocyanate of about 0.9 to 1.2 equivalents per equivalent of the first component of oligomeric aminobenzoic ester or amide or aromatic diamine derivative, based upon the isocyanate groups and amino groups, respectively, of the polyisocyanate and oligomeric aminobenzoic acid ester or amide or diamine derivative reactants. Typically, from about 1.0 to about 1.15 equivalent of polyisocyanate material per equivalent of the first component e.g. oligomeric aminobenzoic acid ester or amide is employed.

Preferably, the primary reactants, e.g. the ester or amide (Formula I), and the polyisocyanate are combined in a volume ratio whereby the isocyanate is in excess to the ester or amide or diamine and is expressed in the following manner:

$$\frac{100}{0.95} \times \frac{1}{\substack{\text{Total Equivalent Weight} \\ \text{of the first component e.g.} \\ \text{the oligomeric ester or amide} \\ \text{(grams/mole equivalent)}}} \times \frac{4200}{\substack{\text{percent volume of} \\ \text{the polyisocyanate} \\ \text{second component}}},$$

which gives the parts of the polyisocyanate per 100 parts of the first reactant e.g. the oligomeric aminobenzoic acid ester or amide.

The amount of stabilizing carrier agent employed is one which is sufficient to dissolve the first reactant, e.g. the oligomeric aminobenzoic acid ester or amide reactant or diamine derivative reactant, and the polyisocyanate second reactant, and maintain the reaction product thereof, i.e., the polyurea, in solution without the precipitation out or gelling of the polyurea product. Typically, the amount of stabilizing carrier employed is about 10 to 80 volume percent of the total reaction solution. Typically the amount of the stabilizing solvent, e.g. aldehyde and/or ketone of formula (6), employed with at least one polyol of formula (9) is in the ratio of 10 to 80 parts of solvent to 1 part of polyol. The amount of stabilizing solvent, e.g., acetone, is adjusted depending upon the viscosity desired for specific application requirements, e.g. for maximum penetration and a desired coating thickness on the treated nail.

Polymerization additives of various types employed in the manufacture of polymeric products can desirably be employed in the stabilized reaction solution. For example, such polymerization agents as ultraviolet absorbers, fillers, plasticizers, etc., can be employed where desired.

Typically a flow and leveling agent polymerization additive is employed. Preferably such additive comprises a glycidyl ester of neo decanoic acid, of the formula

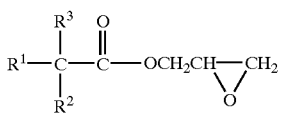

where the $R^1$, $R^2$, $R^3$ are independently of each other H and loweralkyl where the sum of each alkyl group of $R^1$, $R^2$, and $R^3$ does not exceed 8 carbon atoms. Other flow and leveling agents include the diglycidyl ether of 1,4-butane diol, the diglycidyl ether of neopentyl glycol, the polyglycidyl ether of aliphatic polyols, phenyl glycidyl ether, nonyl phenyl glycidyl ether, $C_9$–$C_8$ glycidyl ethers, polyglycidyl ether of castor oil, trimethyol ethane of triglycidyl ether and the ester forms of the aforementioned ethers. These ethers and esters are commercially available from the Shell Chemical Company and are designated as HELOXY products. The glycidyl neodecanoate is commercially available from Exxon Chemical Company and is known as GLYDEXX® N-10.

Specifically, GLYDEXX® N-10 ("N-10") is neodecanoic acid, oxiranyl methyl ester which is a reactive diluent, i.e. a substance which substitutes as a solvent but which is a non-volatile portion of the binder or curative due to its high boiling point of 255° F. and a vapor pressure of 0.11 mmHg at 68° F.

N-10 effects rapid uniform and leveling characteristics to a polymer coating.

Additionally, employed is an ultraviolet (UV) light absorber such as benzotriazoles, e.g. benzotriazoles revealed in U.S. Pat. Nos. 3,004,896 and 3,189,615. Such benzotriazoles are commercially available from Ciba Geigy as Tinuvin® products, such as Tinuvin® P, (2-(2H-benzotriazol-2yl))-4-methylphenol); Tinuvin® 1130, comprising about fifty-two weight percent of poly(oxy-1,2-ethanediyl), α-(3-(3-(2H-benzotriazol-2-yl)-5-(1,1-dimethylethyl)-4-hydroxyphenyl)-1-oxopropyl)-ω-hydroxy, of the formula,

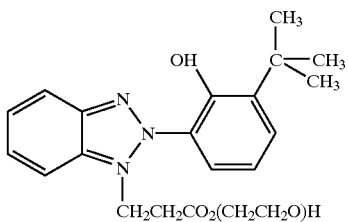

having an average molecular weight of 637, about thirty five weight percent of poly(oxy-1,2-ethanediyl), α-(3-(3-2H-benzotriazole-2-yl)-5-(1,1-dimethylethyl)-4-hydroxyphenyl)1-oxopropyl-ω-(3-(3-2H-benzotriazol-2-yl)-5-(1,1-diamethylethyl)-4-hydroxyphenyl)-1-oxopropyoxy), of the formula,

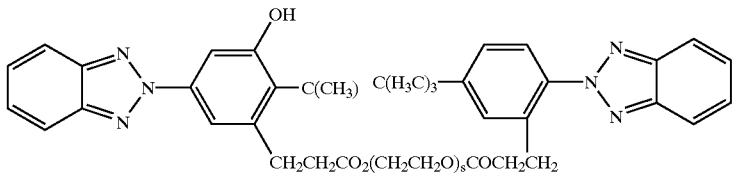

having an average molecular weight of 975, and the remainder (about thirteen weight percent of polyethylene glycol (300 molecular weight), which is used to functionalize the Tinuvin® 1130; Tinuvin® 292 and Tinuvin® 328, [2-(2'-hydroxyl-3,5'-di-tert-amylphenyl)benzotriazole].

Finally, an antioxidant may be employed. A preferred antioxidant is 3,5-di-tert-butyl-4-hydroxycinnamate, known as IRGANOX 1076.

A preferred UV stabilizer/antioxidant additive composition comprises about 70–75 weight percent of Tinuvin® 1130, 10–15 weight percent IRGANOX 1076 and 10–20 weight percent of Tinuvin® 328.

The concentration of the additives, e.g. uv stabilizer, antioxidant, leveling agent, etc. of the total formulation will be varied accordingly in a manner well known to those skilled in the art. Typically, where the reactants are VERSALINK® P-1000 and ISONATE® 2143L, the carrier solvent is acetone and the leveling agent GLYDDEX® N-10 is employed ("FORMULATION"), the polyol component of the stabilizing carrier in the stabilized reaction solution and the FORMULATION is present in an amount which is in the ratio of the oligomeric aminobenzoic acid ester to the polyol of 5 to 2.66 to 1, preferably between 4.25 and 3.75 to 1, and, most preferably 4.0 to 1.

If a mixture of polyols is employed in the FORMULATION, e.g., ethylene glycol ("EG") and propylene glycol ("PPG"), each polyol preferably should be present in equal amounts.

Additionally, typically, for the FORMULATION, the ratio of N-10/2143L is equal to or less than the ratio of EG+PPG/2143L. The ratio range is typically 0.72 to 1.3, preferably 0.85 to 1.15, and most preferably 1.0 for N-10/2143L to EG +PPG/2143L.

Finally, for the FORMULATION, the ratio of EG+N-10/ 2143L to PPG+N-1 012143L is typically 1.

Another ratio which is considered with the FORMULATION is the ratio of EG/N-10 and PPG/N-10 which typically are equal to each other as well as equal to twice that of (EG+PPG)/2143L. Typically, the ratio of EG/N-10 to PPG/N-10 is 0.8 to 1.42, preferably 0.92 to 1.2 and most preferably 1.0.

The stabilized reaction solution can be stored in a sealed container without the reactants reacting until needed. As previously discussed, the stabilized reaction solution is applied to the nail by conventional topical means, to form a liquid film of a desired thickness. The stabilized reaction solution is treated, e.g. by heating, evaporation, etc., to remove at least a portion of the stabilizing carrier to form a solid cured polyurea material which has penetrated into the depth of the nail, and has formed the polyurea coat thereon.

The fact that the stabilizing reaction solution can be applied without reaction spontaneously occurring, permits greater penetration of the stabilized reaction solution into the nail until removal of a portion of the stabilizing carrier is carried out. This is a great advantage in treating nails, e.g. hand or toe of a person desiring or requiring a cosmetic polish or lacquer nail coat.

It is to be noted and stressed that the reaction solution and the stabilized reaction solution, described previously, and the blocked reaction solution to be hereafter described, have the property of chemically binding to skin proteins, and more generally to bodily ones. These reaction solutions and the resultant reaction products, e.g. polyurea, have the capacity of closely binding to the skin through either chemical or physical means, and possess elasticity very similar to that of skin, good abrasion resistance and impermeability to water.

The resultant oligomeric film when applied as a thin film, reacts with and remains bound to the nail, protecting the underlying derma while accelerating regeneration of skin and nail.

In another embodiment for cosmetic treatment of a nail, a blocked reaction solution is employed as the polyurea composition. In particular, the oligomeric polyamino benzoic acid ester or amide of formula I, is selected. Preferably, the compound of formula I is selected from the group consisting of polytetramethyleneglycol-di-p-aminobenzoates, polyethyleneglycol-di-p-aminobenzoates, and polypropyleneglycol-di-p-aminobenzoates.

The compound of formula I is reacted with an aromatic, heterocyclic, sterically hindered or long chain aldehyde to block at least one amino group of compound I.

Preferably, the aromatic aldehydes are represented by the formula (11):

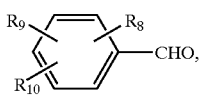
(II)

wherein $R_8$, $R_9$ and $R_{10}$ are hydrogen, halogen, $C_1$–$C_{20}$ alkyl, $C_1$–$C_{20}$ alkoxy, acyloxy, acylamino, or $C_1$–$C_{20}$ alkylthio.

Preferably, the said sterically hindered aldehydes are presented by the formula (12)

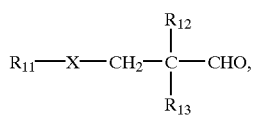
(12)

wherein $R_{11}$ is hydrogen or selected from the group consisting of aryl, substituted aryl, $C_1$–$C_{20}$ alkyl or aralkyl;

$R_{12}$ and $R_{13}$ are $C_1$–$C_6$ alkyl;

X is a covalent bond or selected from —O—, —CH$_2$—, —S—, —NHCOO—, —HNCONH—, —CONH—, —CONR$_{14}$—OR —COO—.

More preferably, the aldehydes are selected form the group consisting of benzaldehyde, anisaldehyde, furfural, ethoxybenzaldehyde, butoxybenzaldehyde, hexyloxybenzaldehyde, octyloxybenzaldehyde, decyloxybenzaldehyde, dodecyloxybenzaldehyde, hexadecyloxybenzaldehyde, ethylbenzaldehyde, isopropylbenzaldehyde and dimethylbenzaldehyde.

The blocked polyaminobenzoates or polyaminobenzamides of formula I of the present invention may be prepared by the following procedure:

The above described polyaminobenzoate or polyaminibenzamide of formula I is heated with an aldehyde to allow a dehydration reaction and the water generated by the reaction is distilled out azeotropically or absorbed by molecular sieves or reacted with a water sponger. These reactions can be carried out with or without a solvent. After completion of the reaction the solvent, if employed, is distilled off from the reaction mixture to obtain the desired aldimine.

The water sponger can be an organic mono- or polyisocyanate.

The resultant blocked polyaminobenzoate or polyaminobenzamide is then combined with the second component, i.e., the polyisocyanate, to form the blocked reaction composition or solution.

Preferably the polyisocyanate is carbodimide modified polyisocyanate, biuret modified polyisocyanate, isocyanurate modified polyisocyanate or urethane modified polyisocyanate.

Preferably the polyisocyanate is derived from a sterically hindered isocyanate.

More preferably the said polyisocyanate is represented by the formulat (13):

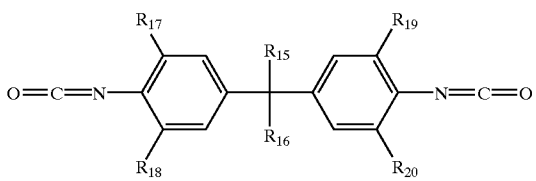
(13)

wherein $R_{15}$ and $R_{16}$ are hydrogen, $C_1$–$C_6$ alkyl or haloalkyl;

$R_{17}$, $R_{18}$, $R_{19}$, $R_{20}$ are hydrogen, halogen, $C_1$–$C_6$ alkyl or $C_1$–$C_6$ alkoxy.

Most preferably the polyisocyanate is an isocyanate-ended polyurethane/urea prepolymer. This prepolymer which has a plurality of iscocyanate groups and can be used for the invention is prepared by reacting the above organic polyisocyanate compound with a known polyol, known polyamine and other known compounds having two or more active hydrogens in a molecule. Free isocyanate groups are remained in the polyurethane prepolymer.

The resultant moisture curable polyurethane composition can be prepared by mixing the polyaldimine with the polyisocyanate and/or the polyurethane prepolymer containing the isocyante groups.

The ratio of the number of amino groups in the polyamine formed by the hydrolysis of the polyaldmine to the number of isocyanate groups contained in the above described polyisocyanate and/or the polyurethane prepolymer having the isocyanate groups is from 0.5 to 2.0, preferably from 0.7 to 1.5.

Further, a catylyst for curing can be incorporated into the blocked reaction composition as well as most solvents to control the viscosity. Suitable inert solvents include hexane, heptane, and octane; ethylacetate, butyl acetate, acetones, methyl ethylketone, methylisobutylketone cellosolve acetate, butyl cellosolve acetate, butiryl cellosolve acetate. These solvents can be used in the range of 50% by weight or less, preferably from 0 to 40% by weight of the composition.

Preferred curing acceleration catalysts include protic acids and phosphate esters. Preferably, the protic acids are carboxylic, sulfonic or phosphonic acids. The amount of these catalysts is in the range of preferably 0.05 to 5% by weight of the composition.

No particular restriction is imposed on the method of blending these components. Simple mixing or mixing by other known methods can be arbitrarily carried out.

When the additives have high moisture content, these additives must previously be dehydrated or addition of a dehydrating agent such as zeolite is required.

The resultant moisture curable blocked reaction composition or solution can be applied immediately to a nail to be treated or the solution can be stored in a sealed container for later usage. Upon application to the nail, as previously described, the liquid film, reacts with the moisture in the atmosphere to cure the polymer to form the polyurea film or composition.

The above-described polyurea compositions i.e. reaction solution, stabilized reaction solution and blocked reaction solution can be combined with physiologically acceptable additives, such as (1) plasticizers, e.g. dialkylphthalates such as butylphthalate; hydroxy fatty acid oils such as castor oil; triglycerides, silicon oils; triactin, propylene glycol, and camphor; (2) film modifiers, which modify the hardness and/or flexibility of the resultant polyurea film, e.g. acrylic ester resins; cullulose derivatives, polyamide resins; (3) surfactants, e.g. polyethylene glycol-alkyl ethers; (4) penetration enhancers, e.g. azole, dimethyl sulfoxide, unsaturated fatty alcohols, propylene glycol, acetates, such as methyl acetate, butylacetate, ethylacetate, isobutyl acetate, isopropylacetate, propylacetate; (4) antioxidants, such as tocopherol; (5) nail softeners and avulsers, such as urea, sulfhydryl agents, sulfur based reducing agents, such as sodium sulfide; (6) for the reaction solution and blocked reaction solution, physiologically acceptable solvents, such as ethanol, isopropanol, acetone, ethyl acetate; (7) u.v. adsorbers, etc.

It has surprisingly been found that when the polyurea composition, selected from (a) the reaction solution, (b) the stabilized reaction solution, (c) the blocked reaction solution or composition, or (d) a mixture of any of the foregoing solutions, is applied to a healthy nail or a nail having onychomycosis, the nail resulting is (1) hardened, thereby alleviating a brittleness condition, and (2) water impermeable, thereby making it ideal for a nail polish or lacquer base to which the nail polish or lacquer is applied. Accordingly, a colored pigment or any additive utilized in the cosmetics industry for fabricating a cosmetic nail coating, or nail polish, can be incorporated into the therapeutic polyurea composition to form the cosmetic nail coating or nail polish.

Additionally, additives common in the cosmetics industry are employed with the polyurea composition to form the cosmetics nail polish or lacquer. Such additives as plasticizers, colorants, pigments, perlescent agents, sedimentation readers, sulfonamide resins, silicates, perfumes, wetting agents, e.g. sodium dioctylsulfosuccinate, lanoline derivatives, sunscreen agents e.g. 2-hydroxy-4-methoxybenzophenone, antibacterials with keratolytic and/or keratoplastic action e.g. aumonium sulfite, esters and salts or thioglucote acid, urea, allantoin, enzymes, salicylic acid, etc., may be employed in a customary fashion of the cosmetics industry to prepare the cosmetic nail polish.

I claim:

1. A method of applying a cosmetic nail lacquer or polish to a nail of an animal, which comprises,
    (a) applying to the exterior surface of the nail an effective amount of a polyurea composition selected from the group consisting of
        (a) a reaction solution;
        (b) a stabilized reaction solution;
        (c) a blocked reaction solution; and
        (d) a mixture of any of the foregoing to form a liquid film thereon; and
    (b) curing said liquid film to form a coat on at least said exterior surface.

2. The method as defined in claim 1 herein
said reaction solution comprises a mixture of a first component comprising
    (a) an oligomeric aminobenzoic acid ester or amide of the formula,

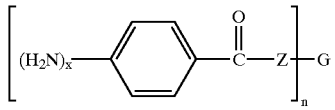

wherein n is an integer from 2 to 4, each x is one or two;
        each benzoyl nucleus is para-, meta or di-metaamino-substituted;
        each Z is —O— or —N—; and G is an n- valent radical obtained by removal of hydroxy groups or amino groups from an n- valent polyol or polyamine having a molecular weight of from about 400 to about 6,000;
    a suitable aromatic diamine or a mixture of the foregoing; combined with
    (b) a second component comprising a polyisocyanate;
        said stabilized reaction solution comprises said first and said second components and further a stabilizing carrier;
        said blocked reaction solution comprises said first component which has at least one of its aromatic amino groups blocked by reaction with an aldehyde prior to combining with said second component.

3. The method as defined in claim 2, wherein said polyurea composition comprises said stabilized reaction solution and wherein said stabilizing carrier comprises a stabilizing solvent and a polyol.

4. The method as defined in claim 3, wherein said stabilizing solvent is selected from the group of
    (a') an aldehyde or ketone of the formula

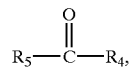

where $R_4$ and $R_5$ are independently of each other hydrogen and lower alkyl or $R_4$ and $R_5$ are joined to form a five or six-membered ring,
    (b') an ester having the formula,

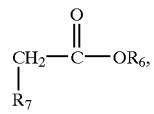

where $R_6$ and $R_7$ are independently loweralkyl and $R_7$ is additionally H and loweralkoxy,
    (c') ortho-, meta- or para-dimethyl benzene,
    (d') N-methyl pyrrolidone,
    (e') Solvesso solvent;
    (f') a petroleum hydrocarbon;
    (g') a lactone of the formula

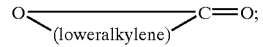

and (h') a mixture of any of the foregoing.

5. The method as defined in claim 4, wherein said stabilizing solvent is acetone.

6. The method as defined in claim 4, wherein said ester (b') comprises an acetate selected from the group consisting of methylacetate, ethylacetate, butylacetate, methoxypropyl acetate or a mixture of any of the foregoing acetates.

7. The method as defined in claim/wherein said polyol is one having the formula

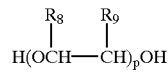

where p is an integer of 1 to 14 and $R_8$ and $R_9$ are independently of each other H and lower alkyl.

8. The method as defined in claim 7, wherein said polyol is one where p is equal to 1 to 3.

9. The method as defined in claim 8, wherein said polyol is one selected from the group consisting of ethylene glycol, propylene glycol, 1-3-butylene glycol, 1-4-butylene glycol, 2-3-butylene glycol and a mixture of any of the foregoing glycols.

10. The method as defined in claim 9, wherein said stabilizing solvent comprises acetone and said polyol comprises a mixture of ethylene glycol and propylene glycol.

11. The method as defined in claim 10, wherein said oligomeric amino benzoic acid amide has the formula

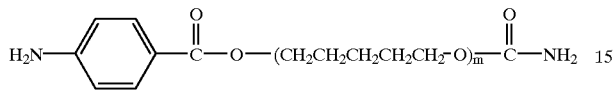

where m is an integer of 13 to 14, with a molecular weight of 1238.

12. The method as defined in claim 2, wherein said polyurea composition comprises said blocked reaction solution, wherein said first component is selected from the group consisting of a polytetramethyleneglycol-di-p-aminobenzoate, a polyethyleneglycol-di-p-aminobenzoate and a polypropyleneglycol-di-p-amino benzoate; and
wherein said aldehyde is selected from the group consisting of aromatic, heterocyclic, sterically hindered and long chain aldehydes.

13. The method as defined in claim 12, wherein said aldehyde has the formula,

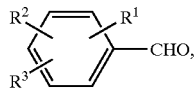

where $R^1$, $R^2$ and $R^3$ are independently of each other, hydrogen, halogen, $C_1$–$C_{20}$ alkyl, $C_1$–$C_{20}$ alkoxy, acyloxy, acylamino or $C_1$–$C_{20}$ alkylthio.

14. The method as defined in claim 12, wherein said aldehyde has the formula,

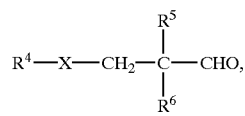

where $R^4$ is aryl, substituted aryl, $C_1$–$C_{20}$ alkyl, aralkyl, hydrogen;

$R^5$ and $R^6$ are $C_1$–$C_6$ alkyl;

X is a covalent bond or is selected from —O—, —$CH_2$—, —S—, —NHCOO—, —NHCONH—, —CONH—, —$CONR^5$ and —COO—.

15. The method as defined in claim 12, wherein said aldehyde is selected from the group consisting of benzaldehyde, anisaldehyde, furfuryl, ethoxybenzaldehyde, butoxybenzaldehyde, hexyl oxybenzaldehyde, octyloxybenzaldehyde, decyloxybenzaldehyde, isopropylbenzaldehyde and dimethylbenzaldehyde.

16. The method as defined in claim 12, wherein said second component has the

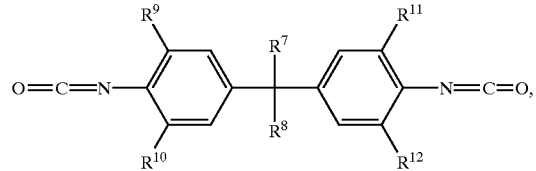

where $R^7$ and $R^8$ are each independent of the other hydrogen, $C_1$–$C_6$ alkyl, haloalkyl; $R^9$, $R^{10}$, $R^{11}$, $R^{12}$ are each independent of one another, hydrogen, halogen $C_1$–$C_6$ alkyl, $C_1$–$C_6$ alkoxy.

17. The method as defined in claim 1, which further comprises, applying a cosmetic nail lacquer or polish to said coat.

\* \* \* \* \*

UNITED STATES PATENT AND TRADEMARK OFFICE
CERTIFICATE OF CORRECTION

PATENT NO. : 6,401,724 B1
DATED : June 11, 2002
INVENTOR(S) : Kenneth I. Sawyer

It is certified that error appears in the above-identified patent and that said Letters Patent is hereby corrected as shown below:

<u>Column 24,</u>
Line 59, delete "claim/" and substitute therefor -- claim 3 --.

Signed and Sealed this

Fifteenth Day of October, 2002

*Attest:*

*Attesting Officer*

JAMES E. ROGAN
*Director of the United States Patent and Trademark Office*